United States Patent
Muller

(10) Patent No.: US 10,401,296 B1
(45) Date of Patent: Sep. 3, 2019

(54) HORIZONTALLY-SCALABLE MICROCAVITY-ENHANCED RAMAN SCATTERING INTEGRATED PLATFORM FOR MULTIGAS CHEMICAL ANALYSIS

(71) Applicant: Andreas Muller, Tampa, FL (US)

(72) Inventor: Andreas Muller, Tampa, FL (US)

(73) Assignee: University of South Florida, Tampa, FL (US)

(*) Notice: Subject to any disclaimer, the term of this patent is extended or adjusted under 35 U.S.C. 154(b) by 848 days.

(21) Appl. No.: 15/065,438

(22) Filed: Mar. 9, 2016

Related U.S. Application Data

(60) Provisional application No. 62/146,714, filed on Apr. 13, 2015.

(51) Int. Cl.
| | | |
|---|---|---|
| *G01N 21/65* | (2006.01) | |
| *G01J 3/02* | (2006.01) | |
| *G01J 3/44* | (2006.01) | |
| *A61B 5/00* | (2006.01) | |
| *A61B 5/1455* | (2006.01) | |

(52) U.S. Cl.
CPC .............. *G01N 21/65* (2013.01); *G01J 3/021* (2013.01); *G01J 3/44* (2013.01); *A61B 5/0075* (2013.01); *A61B 5/1455* (2013.01)

(58) Field of Classification Search
CPC .. G01N 21/65; G01J 3/44; G01J 3/021; A61B 5/1455; A61B 5/0075
See application file for complete search history.

(56) References Cited

U.S. PATENT DOCUMENTS

| | | | |
|---|---|---|---|
| 4,648,714 | A | 3/1987 | Benner et al. |
| 4,784,486 | A | 11/1988 | Van Wagenen et al. |
| 5,255,067 | A | 10/1993 | Carrabba et al. |
| 8,599,373 | B1 | 12/2013 | Djeu et al. |
| 8,736,835 | B2 | 5/2014 | Djeu et al. |

OTHER PUBLICATIONS

Kippenberg et al., Theoretical and Experimental Study of Stimulated and Cascaded Raman Scattering in Ultrahigh-Q Optical Microcavities. IEEE Journal of Selected Topics in Quantum Electronics. 2004. vol. 10 (No. 5): 1219-1228.

Li et al., Near-confocal cavity-enhanced Raman spectroscopy for multitrace-gas detection. Optics Letters. 2008. vol. 33 (No. 18): 2143-2145.

Linder et al., 900 mW continuous wave operation of AlInGaP tapered lasers and superluminescent diodes at 640 nm. Lasers and Electro-Optics. 2004: 900-901.

Moore. Recent Advances in Trace Explosives Detection Instrumentation. Sensing and Imaging. 2007. vol. 8:9-38.

Petrak et al., Purcell Enhanced Raman Scattering from Atmospheric Gases in a High-Finesse Microcavity. Phys. Rev. A. 2014. vol. 89: 023811.

(Continued)

*Primary Examiner* — Hina F Ayub
(74) *Attorney, Agent, or Firm* — Nilay J. Choksi; Smith & Hopen, P.A.

(57) ABSTRACT

An integrated approach to optical sensing (~$cm^3$ excluding electronics) at concentrations of parts-per-million or less (ppm). The invention enables the trace detection of chemicals in fluids (gas or liquid) in a highly integrated package. The simultaneous detection of any number of Raman active molecular species (including isotopes) may be achieved in a scalable, low-cost manner.

18 Claims, 5 Drawing Sheets

(56) References Cited

OTHER PUBLICATIONS

Petrak et al., Coherent Anti-Stokes Raman Scattering in a High-Finesse Microcavity. Opt. Express. 2014. vol. 22 (No. 18): 21999.

Muller et al., High Q (33 000) all-epitaxial microcavity for quantum dot vertical-cavity surface-emitting lasers and quantum light sources. Appl. Phys. Lett. 2006. vol. 88: 031107.

Zhao et al., Buried heterostructure vertical-cavity surface-emitting laser with semiconductor mirrors. Appl. Phys. Lett. 2012. vol. 101: 101103.

Muller et al., Self-Aligned All-Epitaxial Microcavity for Cavity-QED with Quantum Dots. Nano Lett. 2006. vol. 6 (No. 12): 2920-2924.

Muller et al., Ultrahigh-finesse, low-mode-volume Fabry-Perot microcavity. Optics Lett. 2010. vol. 35 (No. 13): 2293-2295.

Muller et al., Coupling an epitaxial quantum dot to a fiber-based external-mirror microcavity. Appl. Phys. Lett. 2009. vol. 95: 173101.

Martin et al., Single-Particle Aerosol Mass Spectrometry for the Detection and Identification of Chemical Warfare Agent Simulants. Analytical Chemistry. 2007. vol. 79: 6368-6375.

McGill et al., The "NRL-Sawrhino": a nose for toxic gases. Sensors and Actuators B. 2000. vol. 65: 10-13.

Yariv. Quantum Electronics. 3rd edition. John Wiley & Sons, Inc. New York, NY. 1989:1-693.

Cairo et al, QED-vacuum confinement of inelastic quantum scattering at optical frequencies: A new perspective in Raman spectroscopy. Phys. Rev. Lett. 1993. vol. 70 (No. 10): 1413-1416.

Fainstein and Jusserand. Phonons in semiconductor planar microcavities: A Raman scattering study. Phys. Rev. B: 1996. vol. 54 (No. 16): 11505-11516.

Colombe et al., Strong atom-field coupling for Bose-Einstein condensates in an optical cavity on a chip. Nature. 2007. vol. 450 (No. 8): 272-277.

Xu et al., Spectroscopy of Single Hemoglobin Molecules by Surface Enhanced Raman Scattering. Phys. Rev. Lett. 1999.vol. 83 (No. 21): 4357-4360.

Zaitsu et al., Phase-Matched Raman-Resonant Four-Wave Mixing in a Dispersion-Compensated High-Finesse Optical Cavity. Phys. Rev. Lett. 2008. vol. 100: 073901.

Mangold et al., Vecsel gain characterization. Opt. Express. 2012. vol. 20 (No. 4): 4136-4148.

Petrak et al., Feedback-controlled laser fabrication of micromirror substrates. Rev. Sci. Instrum. 2011. vol. 82: 123112.

HORIZONTALLY-SCALABLE MICROCAVITY-ENHANCED RAMAN SCATTERING INTEGRATED PLATFORM FOR MULTIGAS CHEMICAL ANALYSIS

CROSS-REFERENCE TO RELATED APPLICATIONS

This nonprovisional application is a continuation of and claims priority to U.S. Provisional Patent Application No. 62/146,714, entitled "Integrated Detection Array Based on Microcavity-Enhanced Coherent Anti-Stokes Raman Scattering", filed Apr. 13, 2015, the entirety of which is incorporated herein by reference.

OTHER RELATED APPLICATIONS

This nonprovisional application is also related to U.S. Pat. Nos. 8,599,373 and 8,736,835, both of which are incorporated herein by reference in their entireties.

BACKGROUND OF THE INVENTION

1. Field of the Invention

This invention relates, generally, to detection arrays. More specifically, it relates to an integrated microcavity-enhanced molecular detection array.

2. Brief Description of the Prior Art

Trace sensing has a long history of applications in defense, air quality control, and precision metrology [4]. Yet, today, there is no versatile off-the-shelf chip-scale chemical sensor (gas or liquid) that may be adequate, for example, for integration into a portable electronic device such as a cell phone. Currently the most widely used trace gas analyzers employ ion mobility spectrometry (IMS) in which substances are ionized and their mass-dependent drift velocity through a buffer gas is measured [10]. IMS offers ppm-level sensitivity, good chemical specificity, and fast response but has a relatively high cost, complexity and footprint. Most alternative low-cost trace gas sensors today rely on high frequency mechanical resonators coated with chemo-selective material [11]. Minute mass changes can be recorded, yielding parts-per-trillion (ppt) sensitivity, but with poor selectivity and reliability, since a number of chemicals can attach to the same chemical receptor. Optical trace detection methods such as tunable diode laser spectroscopy (TDLS) and cavity ring-down spectroscopy (CRDS) are highly specific, but use large and expensive multi-pass absorption cells, and tunable stabilized laser sources are needed.

Raman spectroscopy, on the other hand, in which the vibrational fingerprint of a given multi-atomic gas is detected at optical frequencies, is highly specific, and inexpensive optical components may be used. However, the free-space Raman scattering cross-section for most gases and liquids is so small (on the order of $10^{-31}$ cm$^2$/sr-molecule [12]) that a compact device for trace detection has not been demonstrated yet.

The rate of Raman scattering can nonetheless be significantly increased by the use of a microcavity, which quantizes the electromagnetic field, thus altering the rate of spontaneous emission into a specific cavity mode. This Purcell effect for Raman scattering was first demonstrated by Cairo et al. [13]. By also making the pump laser resonant with the cavity, a further increase in signal can be obtained [14]. The current inventor recently achieved the implementation of such a double resonance for gases, by harnessing the ultrahigh finesse of laser-fabricated micromirror Fabry-Perot microcavities [1], depicted in FIG. 1A. Its key feature is that it enables fluids to freely flow in its interior while providing ultrahigh finesse at very small dimensions ~1-10 microns. The finesse, F, can be on the order of 100,000 or higher [15] provided that: (i) curved micromirrors are used, and (ii) the mirror surfaces are ultrasmooth, i.e., losses in each mirror are on the order of 100 ppm or less.

Laser microfabrication, as first demonstrated by Reichel et al. [16] can achieve the needed smoothness, and deposited ion-beam-sputtered (IBS) coatings enable a reflectivity R>99.998% together with resilience and durability. For such a reflectivity, an in-coupled beam of power $P_{in}$=2 mW will create a circulating power of $P_{circ}=P_{in}/(1-R)$=100 W. Note that even with the small cavity waists (~1 micron) established in these microcavities, the resulting intensities (~GW/cm$^2$) are far from damage thresholds. In fact, the current inventor has operated the same mirrors in microcavities with a peak finesse of 50,000 under ambient conditions, without observing any degradation for over 3 years.

Combining the circulating laser intensity with the Purcell Raman emission enhancement effect can lead to overall enhancements of Raman scattering signals by 7 orders of magnitude compared to emission into the same solid angle in free space [1]. As an example of the potential of this approach, the measurement of microcavity-enhanced Raman scattering at the 1388.15 cm$^{-1}$ vibrational shift in $CO_2$ under ambient conditions is shown in FIG. 1B. It should be noted that this enhancement is unrelated to surface-enhanced Raman scattering (SERS), which can detect single molecules when adsorbed to nanoparticles [17].

By making use of additional cavity resonances, a whole family of optical processes can be enhanced in microcavities. In particular, with two laser fields (pump and Stokes) resonant with the cavity, a four-wave mixing signal (third-order optical nonlinearity) can be generated at a third resonance. This effect has been demonstrated in large, cm-long open resonators [18], in which a macroscopic coherent anti-Stokes Raman scattering (CARS) signal was obtained from $H_2$ gas (rotational Raman). In microcavities, it has been recently demonstrated that the enhancement of CARS is also possible [2].

However, for practical applications, in particular for low-cost trace sensing, the drawback of all above-mentioned approaches is that expensive external lasers are needed. Moreover, these lasers typically need to be coupled into resonators in a highly precise manner and connected to a feedback system to maintain resonance. As such, it can be seen that conventional Raman-based trace sensors are ineffective, too cost-inefficient and too bulky to be fitted routinely on field personnel or on portable instrumentation.

In U.S. Pat. No. 8,599,373 issued to the current inventor (the '373 patent), a microcavity-enhanced Raman sensor based on a single microcavity was described. There, as well as in a subsequent publication [B. Petrak, N. Djeu, and A. Muller, "Purcell Enhanced Raman Scattering from Atmospheric Gases in a High-Finesse Microcavity", Phys. Rev. A 89, 023811 (2014)], it was shown that Raman scattering from fluids can be dramatically enhanced by the use of a doubly-resonant high-finesse microresonator (one resonance at the pump laser frequency, another at the Stokes emission frequency). For most gases and liquids, with a laser input power of order 10 mW, a cavity finesse of 50000, a cavity length of order 10 micrometer, and a measurement duration of order 1 min, this translates into theoretical detection limits of order 1-10 ppm (parts-per-million) for a single specific gas (single Raman shift) at a time.

In practical applications, simultaneous multigas (an ensemble of Raman shifts) detection is often desired. In addition, a detection limit into the ppb (part-per-billion) range is advantageous. However, ppb detection sensitivities are not likely to be achievable in a single cavity configuration because of material and fabrication limitations. For example, damage thresholds of coatings in a single cavity configuration limit a substantial increase in pump power. Finally, a scalable geometry similar to that found in conventional lateral electronic circuit fabrication is in general called for to obtain a compact and low-cost chemical sensor.

Accordingly, what is needed is a low-cost trace sensing approach that does not require a specialized external laser (i.e., a high-power, stabilized and frequency tunable laser system), is capable of sensing at parts-per-million or less for many chemical species, does not require additional spectroscopic instruments (such as a grating spectrometer), and is highly compact. However, in view of the art considered as a whole at the time the present invention was made, it was not obvious to those of ordinary skill in the field of this invention how the shortcomings of the prior art could be overcome.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an accurate integrated chemical sensing platform is now met by a new, useful, and nonobvious invention.

In certain embodiments, the current invention is a Raman sensor for chemical analysis of a fluid (e.g., liquid or gas), where the concentration of multiple chemical species of interest can be detected simultaneously. The sensor includes a first high-reflector mirror placed in close proximity (within a distance of order 1-10 microns) of a second high-reflector micromirror array. The first high-reflector includes a substantially planar surface coated with a set of low-loss, high-reflectivity dielectric layers. The second high-reflector includes an array of concave micro-templates (of order 10 microns in lateral extent) coated with a set of low-loss, high-reflectivity dielectric layers, where the radius of curvature of the concave surfaces should not exceed the distance between the concave mirrors. The flat reflective surface facing the concave reflective surface at each site of the array create an ensemble of stable optical microcavities (optical resonators), as long as the mirror separation does not exceed the radius of curvature of the concave surface.

A longitudinal extent of the planar side is substantially parallel to a longitudinal extent of the curved side. The dielectric coatings on the first and second reflector surfaces have a high reflectivity (R>99.9%) at both the pump laser's frequency, and at the frequency of the Raman-shifted signal of a given chemical species of interest (typical Raman shifts are of order 1000 $cm^{-1}$). The sample to be analyzed is either placed in or flowed continuously through the gap between the first high-reflector and the second micromirror array reflector. The width of this gap and thus the length of each microcavity in the array may be adjustable piezoelectrically.

The Raman sensor further includes an excitation laser positioned to emit a light beam incident upon the planar micromirror and each curved micromirror. Further, an imaging detector is positioned to receive the array of Raman shifted emission signals in order to detect a concentration of the species of interest within the sample in the channel.

The Raman sensor may further include a laser focusing component positioned between the excitation laser and the planar micromirror to focus or mode match the light through the microcavities. An example of this laser focusing component is a microlens array. Alternatively or in addition, the Raman sensor may include a secondary filter that removes any residual laser pump light between the micromirrors and the Raman emission signal detector.

In other embodiments, the current invention may include any one or more, or even all, of the foregoing characteristics and limitations.

It is an object of an embodiment of the current invention to provide a scalable design and fabrication of integrated molecular sensing platform for fluids at trace concentrations that can be mass-manufactured.

It is an object of an embodiment of the current invention to address the current lack of low-cost compact (~$cm^3$) gas/liquid chemical trace sensor that is durable and fieldable.

It is an object of an embodiment of the current invention to provide advantages over the conventional art, including but not limited to, true chemical fingerprinting (based on rovibrational spontaneous Raman scattering or coherent anti-Stokes Raman scattering), use of minute sample quantities (~$mm^3$), no requirement of external lasers or external moving parts (coherent waves needed for producing the sensing signal may be generated inside of chip), and insensitivity to vibrations and no stabilization needs.

It is an object of the current invention to transform the current paradigm of trace detection by offering: (i) ultrahigh chemical specificity (molecular vibration based), (ii) ultrahigh sensitivity (~parts-per-million or less) (iii) scalability (planar semiconductor/dielectric fabrication), (iv) compactness (~1 $cm^3$ excluding electronics), (v) durability (no consumable components), and (vi) cost efficiency, while necessitating only minute amounts of sample quantities (~$mm^3$). These features are enabled by a unique multidimensional implementation that combines CCD imaging and ultrahigh finesse microcavity length modulation to obtain spectral resolution in the GHz range without requiring spatial beam propagation, frequency stabilization, or additional spectroscopic equipment.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1A:
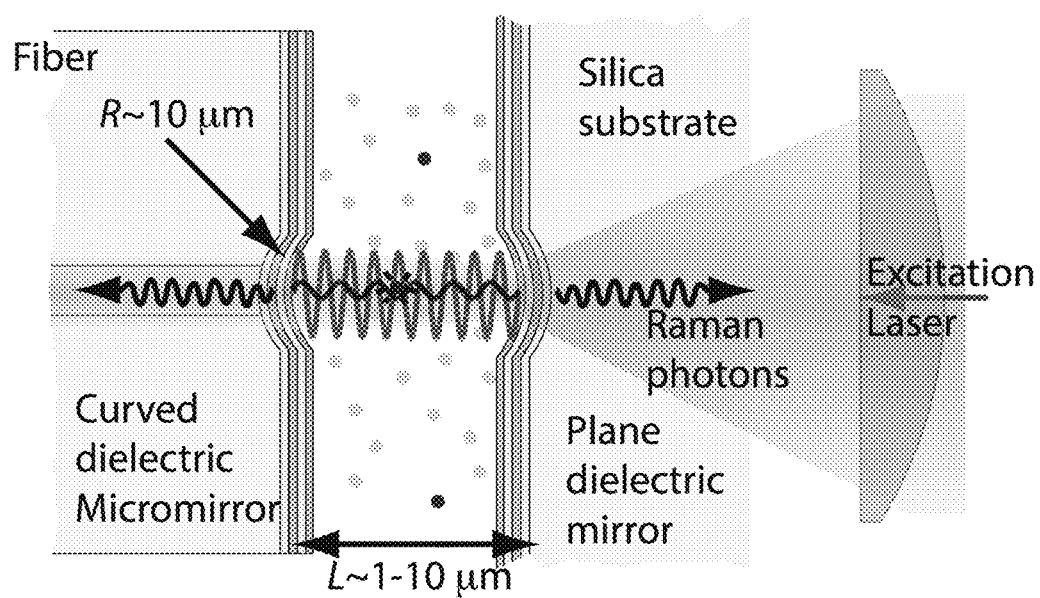
FIG. 1A is a schematic of a curved micromirror based microcavity with typical dimensions.
Figure 1B:
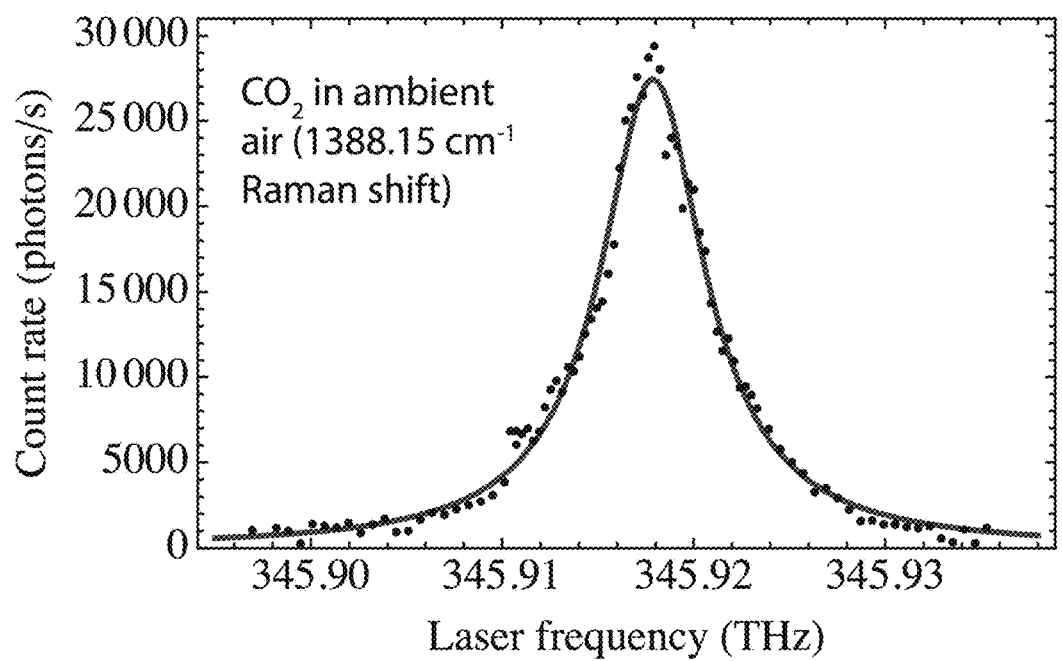
FIG. 1B depicts Purcell-enhanced measurement of $CO_2$ gas Raman signal under ambient conditions (400 ppm) using a doubly-resonant cavity of FIG. 1A.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

The current invention is an improvement over the '373 patent and over U.S. Pat. No. 8,736,835 issued to the current inventor (the '835 patent), both of which are incorporated herein by reference in their entireties. In contrast to the '373 and '835 patents, the instant invention permits horizontal scaling into a multigas analyzer. Generally, the current invention is based on microcavities densely fabricated into arrays, in which imaging and image processing is used to retrieve the concentrations of one or more chemical species in a fluid being tested.

Such a realization is not an obvious, straightforward extension of the previously disclosed single-cavity invention in the '373 and '835 patents, due to the fact that high-finesse cavities fabricated in a large ensemble will unavoidably each have slightly different resonance frequencies, whether it is because of coating non-uniformities or template fabrication non-uniformities. For a large ensemble of microcavities in an array—for example ~10,000-1,000,000 microcavities on a 1 $cm^2$ area with pitch ~50 microns—it is not realistic to match frequencies of individual lasers to each cavity, and thus, the deterministic double-resonance scheme described in the '373 and '835 patents for a single cavity is inadequate. It is an object of the current invention to overcome these drawbacks while providing for a horizontally-scaled, accurate, multifluid analyzer.

For a large enough ensemble of microcavities, one can expect a quasi-continuous distribution of resonance frequencies and free spectral ranges centered around a mean value. A stochastic approach is thus preferred and used herein, which, as will be discussed further, can be realized with an appropriate Raman emission signal detector, such as a charge-coupled device (CCD), with suitable image processing and appropriate "training" algorithms. By virtue of the distribution of cavity resonance frequencies, and thus doubly-resonant Raman shifts, this configuration and methodology can then simultaneously sense a wide range of chemical constituents, including isotopologues, so long as they possess Raman fingerprint lines that fall within the random distribution of cavity double resonances. Furthermore, with this approach, the detection limit scales inversely with the surface area of the array, thus potentially reaching ppb detection limits.

Figure 2A:
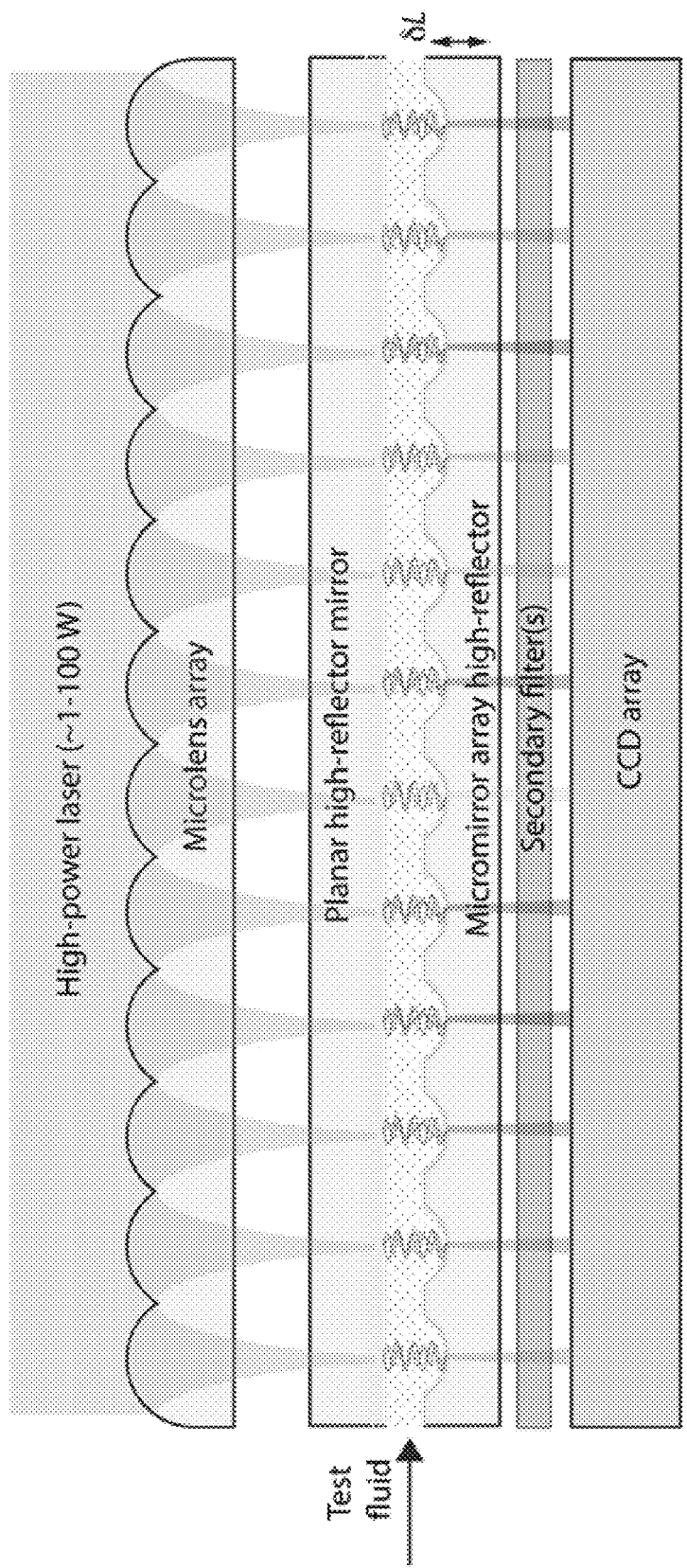
FIG. 2A is a cross-sectional schematic view of a detection array or sending platform, according to an embodiment of the current invention.

Now referring specifically to FIG. 2A, an array of microcavities can be created by the combination of one (1) planar semiconductor mirror and an array of dielectric curved concave micromirrors, where typically the radius of the curvature does not exceed the distance between adjacent micromirrors. Gain layers (quantum wells or quantum dots) grown within the semiconductor mirror, together with a non-resonant excitation laser (whose exact wavelength is non-critical), ensure that the microcavities sustain lasing at their $TEM_{00}$ fundamental transverse modes.

Due to unavoidable fabrication in homogeneities, each cavity in the array can lase at a unique set of frequencies for a given position of the dielectric mirror chip relative to the semiconductor mirror chip (adjusted piezoelectrically). Thus, by scanning this separation, each microcavity can realize a piecewise continuous set of free-spectral-ranges (FSRs), that is, a "pump" standing wave and a "Stokes" standing wave, separated by a given frequency. If this frequency matches the (vibrational) Raman shift of a particular molecule in the fluid, then an "anti-Stokes" wave can be generated. With the correct design of optical coatings, this anti-Stokes wave can be extracted and detected on the CCD.

The magnitude of this signal can be substantial even for a low molecular concentration. It is significantly enhanced by the microcavity for several reasons. First, the circulating power at each mode can be in the tens of Watts, even though the received excitation power per cavity may only be several milliWatts. Second, even with a modest reflectivity at the anti-Stokes frequency, a sizeable Purcell effect may be achieved, thus enabling a collection enhancement. Third, when scanning the separation between the dielectric and semiconductor chips, each cavity in the array will, on average, match a given Raman shift. Thus, proper image processing can yield a signal with a magnitude that scales with the number of microcavities in the array.

Specifically, assuming a $\Delta L = \lambda/20$ RMS cavity length dispersion over the assembled chip (so that for all cavities in the array 5<L<5.04 microns at a given point in the length scan), yields a cavity free spectral range (and thus a measured Raman shift) dispersion of $$\frac{c}{2L} - \frac{c}{2(L+\Delta L)} = 60 \text{ GHz } (2 \text{ cm}^{-1}).$$

Thus, for a Raman linewidth of 1 GHz (typical for gases) out of the ~40,000 microcavities in the array more than 500 can generate a CARS signal then totaling $P_{CARS,total} > 1$ pW at 10 ppm concentration, thus providing the enhanced Raman signal.

In use, the instant methodology and integrated device can continuously monitor the chemical environment (gas or liquid) across a range of applications (e.g., battlefield, medical, homeland security) at parts-per-million or less. More specifically, these applications can include, but are not limited to, hazards sensing (toxic gases, chocking agents, nerve agents, explosive agents, etc.), medical detection (for example for continuous breath), civilian monitoring at airports, quality control, etc., among other suitable applications.

Sensing Platform

FIG. 2A illustrates schematically an arrangement of micro resonators, viewed in a vertical cross section. Structurally, the arrangement includes a laser source, a focusing element such as a microlens array (for optimal power use), a planar microcavity array, an array of dielectric curved micromirrors, optional filters to help remove any residual laser pump light if necessary, and a charge-coupled device (CCD) array as a two-dimensional detector. The fluid to be analyzed flows within the small gap (~1-10 micrometers) between the microcavity array interiors in the direction indicated by "test fluid" in FIG. 2A. The gap spacing is tunable piezoelectrically.

Common to all embodiments is the use of a stochastic imaging approach to retrieve concentration information in a particular sample fluid. Unlike the "deterministic" single cavity approach as seen in the conventional art, the stochastic approach makes no assumptions on prior knowledge of exact cavity resonance frequencies or even the exact frequency of the laser. Instead, it relies on the fact that when an ensemble of individual microresonators is large enough, there will be at least a subset of resonators resonant with the laser frequency and doubly-resonant with a particular Raman shift. This subset will be seen on the CCD image recorded for a given gap setting. By scanning the gap and/or the laser frequency, the subset can be varied, thus giving rise to data stacks of the kind depicted in FIG. 2B.

For most common applications, such as trace sensing in air, it can be assumed that one dominant Raman scattering feature is always present. One or several such features can be used as a reference for calibration. For the latter example for air, the 2330 $cm^{-1}$ line in $N_2$ could be used. In addition, with the help of a fast image processing algorithm and test measurements with known gas mixtures, it is possible to obtain general retrieval of any Raman signature through image searching and interpolation.

Coherent-Anti-Stokes Raman Scattering

Figure 2B:
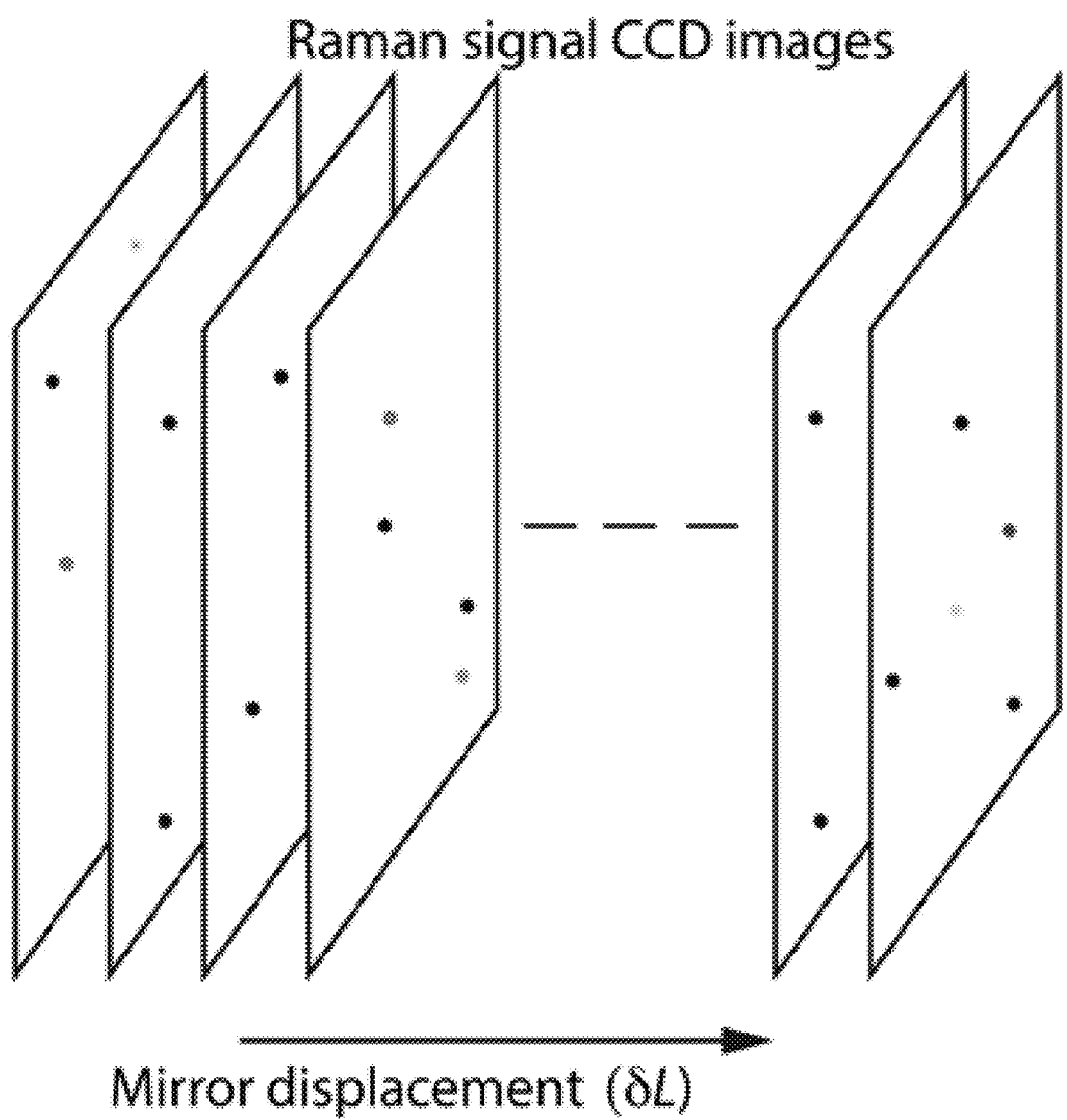
FIG. 2B is a diagram of 2D CCD image stack resulting from scanning the separation between the two high-reflector mirrors (i.e., the semiconductor mirror chip and the dielectric micromirror array chip). Image processing retrieves signal as a measure of concentration.

In an embodiment, the current invention is a sensing platform, and method of use thereof, utilizing microcavity technology that can then be used to significantly enhance a four-wave-mixing chemical fingerprint signal (coherent-anti-Stokes Raman scattering, or CARS) from an ensemble of trace chemical agents in a fluid. Central to the sensor is the implementation of resonant microcavity-enhanced CARS as indicated in FIGS. 2A-2B.

This embodiment includes a planar scalable implementation of microcavity-enhanced CARS. Pump and Stokes waves can be generated at all times (each microcavity acts as open tunable VECSEL) using non-resonant planar excitation and gain-integrated high-reflector. An array of curved micromirrors creates ultrahigh finesse (F>100000) microcavities so that pump and Stokes waves circulating powers are of order 10-100 Watt with only mW supplied. Anti-Stokes sensing signal is Purcell-enhanced by the microcavities, and the CCD with image processing algorithm can retrieve the composition, or species therein.

The problem of using external lasers is addressed by generating the high power optical waves directly inside the microcavity by replacing one of the dielectric mirrors with a semiconductor high-reflector that also integrates a gain medium. Thus, the resulting system acts as a VECSEL [19], but with a mirror spacing of only micrometers (as opposed to traditional cm-long VECSEL cavities). Micrometer-scale mirror separation translates into a resonator spectral mode separation of ~1000 $cm^{-1}$, which is on the same scale as molecular vibrational frequencies. The result is a structure that permanently lases internally at specific frequencies, set piezoelectrically via a spacing (this light does not ever need to be coupled out of the chip), thus always generating a CARS signal if the mode spacing matches a given molecule's Raman shift.

EMBODIMENTS

Using the current invention, no separate spectral analyzer is needed (unlike in conventional spontaneous Raman scattering spectroscopy).

Further, the fluid being tested may be under pressure due to the small areas and volumes (causing only very small forces). This enables a straightforward concentration of the sample under test. For example, since volumes in the microliter-milliliter range are generally sufficient, the limit of detection can be decreased by, e.g., one order of magnitude, by simply compressing the fluid under test by an order of magnitude using methods that may be as simple as a handheld syringe.

Additionally, the chemical species may be isotopically resolved, i.e., isotopologues of the sample molecule, differing by as little as a single neutron, can be differentiated because of unique Raman fingerprints (unique rovibrational spectrum of molecule).

The implementation of a sensing platform may be achieved using various embodiments with differing degrees of complexity and each featuring various advantages.

Embodiment 1: External Pump Laser, Microcavity Spontaneous Raman Array Enhancement In an embodiment of the current invention, an external laser is supplied as the Raman "pump". This laser may be a single high power laser, or a laser array, such as a high-power vertical-cavity surface-emitting laser (VECSEL) array, which can be compact and inexpensive. The laser frequency (or frequencies) may be variable, and a Stokes-shifted doubly resonant Raman signal image stack is recorded on the CCD.

Embodiment 2: Internal Pump Laser, Microcavity Spontaneous Raman Array Enhancement In a slightly more complex embodiment, an active layer is part of the microcavity array coating, for example in the form of a semiconductor gain layer (typically Indium Gallium Arsenide (InGaAs) if in the near-infrared spectral region). The external laser is then a non-resonant excitation laser, the exact frequency of which is unimportant. The non-resonant excitation laser causes lasing at a microcavity mode. Note that the excitation may also be done electrically. The lasing microcavity mode is then the Raman "pump" laser, which generates a Raman signal directly inside the microcavity array. This approach may potentially be more energy efficient, since the laser light at the pump mode need never be coupled out of the cavity, and lasing can occur over a large range of cavity lengths at all times.

Embodiment 3: External Laser, Microcavity CARS Array Enhancement

Using coherent anti-Stokes Raman scattering (CARS) instead of spontaneous Raman scattering, it is possible to provide additional sensitivity and selectivity but likely at a higher complexity. In particular, for CARS, a second laser at the Stokes frequency is utilized. This Stokes laser may be a single high power laser, or a laser array, such as a high-power vertical-cavity surface-emitting laser (VECSEL) array, which can be compact and inexpensive. It is present in addition to the pump laser at the "pump" frequency. By applying a coupled-mode analysis [12], it is found that the power of anti-Stokes radiation, $P_{CARS}$, in Watts, generated in a cavity of finesse $F_{AS}$ at the anti-Stokes frequency, can be approximated by $$P_{CARS} = \frac{\lambda_S^6 \lambda_P^6}{h^2 c^2 \pi^3 \lambda_{AS}^2} \frac{L^4 F_{AS} N^2}{V_{\mathit{eff}}^2 \Delta v_R^2} \left(\frac{d\sigma}{d\Omega}\right)^2 P_{circ,P}^2 P_{circ,S},$$

where L is the cavity length, $\lambda_P$, $\lambda_S$, $\lambda_{AS}$ are the wavelengths of pump, Stokes, and anti-Stokes waves, N is the molecular number concentration, $d\sigma/d\Omega$ is the Raman scattering cross-section, $\Delta v_R$ is the Raman linewidth (in Hz), and $V_{\mathit{eff}}$ is the effective mode volume of the microcavity. Finally, $P_{circ,P}$, $P_{circ,S}$ are the circulating powers at the pump and Stokes modes, respectively. For the 1388.15 cm$^{-1}$ vibrational transition in $CO_2$ at 10 ppm concentration with $F_{AS}=1000$, L=5 μm and $P_{circ,P}=P_{circ,S}=100$ W, this gives $P_{CARS}=3$ fW for an individual microcavity. This power (about 10,000 photons/second) is easily measured with low noise by an uncooled CCD detector.

Embodiment 4: Internal Laser, Microcavity CARS Array Enhancement

Similar to Embodiment 3, the Stokes laser may also be generated internally by a gain layer deposited with the mirror. The external laser is then a non-resonant excitation laser that provides gain for both an internal "pump" laser and an internal "Stokes" laser. The CARS signal is then generated at the anti-Stokes frequency in the form of image stacks as discussed above. Neither the pump nor the Stokes laser need be coupled out of the cavity, providing overall better energy efficiency, i.e., overall the device would use very little power.

Figure 3:
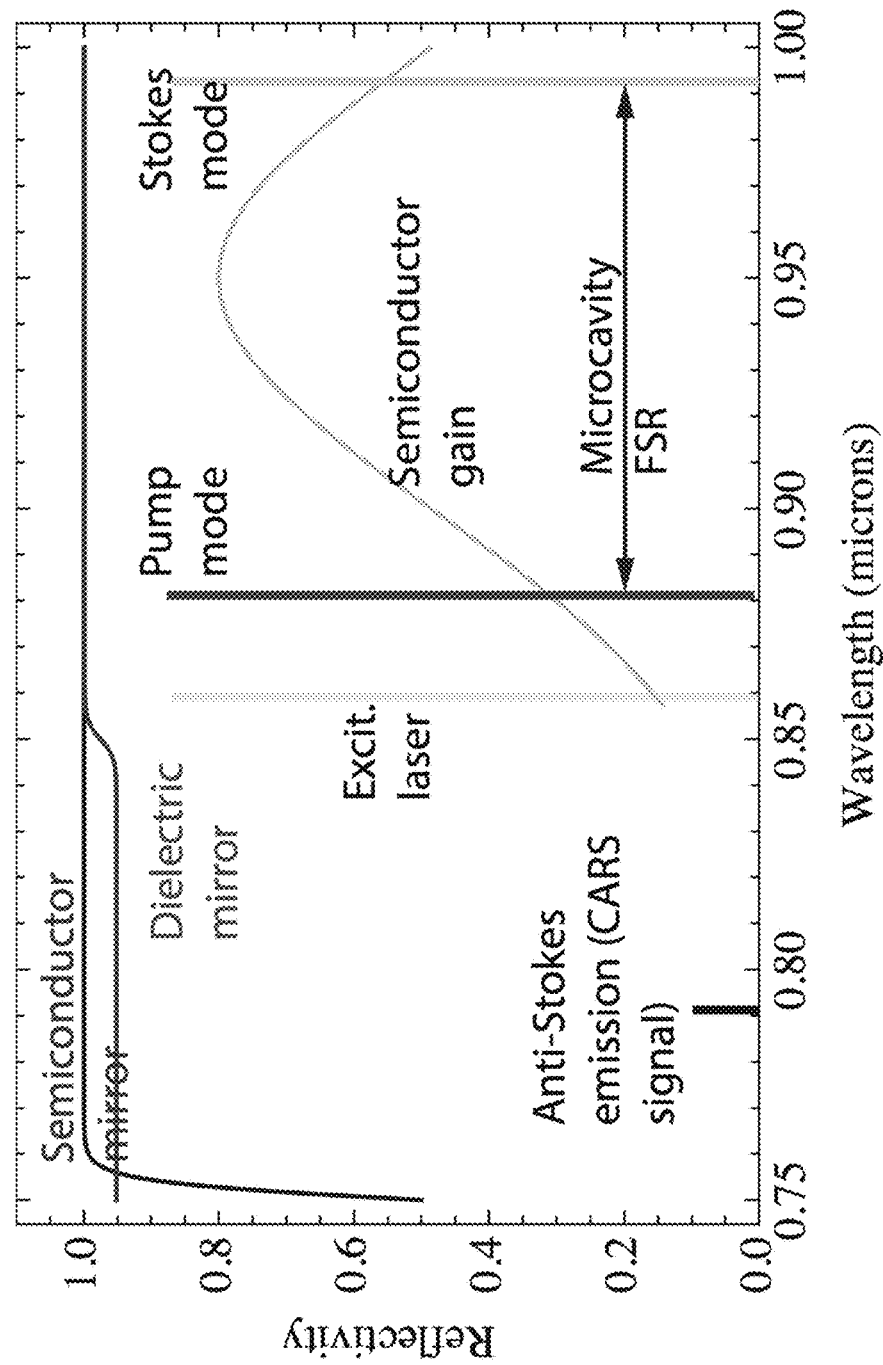
FIG. 3 is a spectral view of an exemplary embodiment including cavity modes, excitation laser, and coating bands.

FIG. 3 depicts a specific example of this embodiment, in particular the spectral arrangement of reflective coating bands for the mirrors (left axis), and example spectral positions of semiconductor gain band, cavity modes, and excitation laser. This arrangement is relevant to Embodiment 4, in that a non-resonant excitation laser creates a population inversion in a gain layer in the semiconductor mirror coating. Lasing occurs at both a "pump" mode and a "Stokes" mode inside the cavity due to the gain and high reflectivity mirrors. A coherent anti-Stokes Raman scattering signal is then generated by the sample gas at an "anti-Stokes" mode (at a higher frequency) to be detected by the CCD as a measure of gas species concentration.

Study/Experiment

An object of this study was to engineer a sensing platform that utilizes of microcavity technology to significantly enhance a four-wave-mixing chemical fingerprint signal (CARS) from an ensemble of trace chemical agents in a fluid. At the heart of the study presented herein is the implementation of resonant microcavity-enhanced CARS in the form illustrated in FIGS. 2A-2B. An array of microcavities is created by the combination of one planar semiconductor mirror and an array of dielectric curved micromirrors. Gain layers (quantum wells or quantum dots) grown within the semiconductor mirror, together with a non-resonant excitation laser (whose exact wavelength is non-critical), ensure that the microcavities sustain lasing at their $TEM_{00}$ fundamental transverse modes.

Each cavity in the array can lase at a slightly different but unique set of frequencies for a given position of the dielectric mirror chip relative to the semiconductor mirror chip (adjusted piezoelectrically). Thus, by scanning this separation, each microcavity can realize a piecewise continuous set of "pump" and "Stokes" standing waves, separated by a given frequency. If this frequency matches the (vibrational) Raman shift of a particular molecule in the fluid, then an "anti-Stokes" wave can be generated. With the correct design of optical coatings, this anti-Stokes wave can be extracted and detected on the CCD as a measure of a particular molecule's concentration.

The magnitude of this signal, analyzed further below, can be substantial even for a low fluid concentration. It is significantly enhanced by the microcavity due to ultrahigh circulating power at each mode combined with the Purcell collection enhancement at the anti-Stokes frequency [1, 2]. Furthermore, with sufficient fabrication homogeneity a substantial fraction of the microcavities in the array can match the same or a very similar Raman shift for a given position. Thus, proper image processing can yield a signal with a magnitude that scales with the number of microcavities in the array.

Recently, a research group associated with the current inventor has proposed [8, 9] and demonstrated experimentally [1, 2] the physical processes that are related to the study presented herein. These include both Purcell-enhanced spontaneous Raman scattering [1] and degenerate coherent anti-Stokes Raman scattering (CARS) in individual microcavities [2]. These publications [1, 2, 8, 9] are incorporated herein by reference in their entireties.

For initial fabrication, a risk-mitigating phased approach was used, in which system complexity was gradually increased, though one of ordinary skill in the art would understand that this approach may not be necessary to fabricate the system or any component thereof described herein. Methodologically, a microcavity sensor array can be designed and fabricated first at low micromirror density (pitch >100 microns) and low cavity finesse at the anti-Stokes wavelength (Fas~1-10). Subsequently, the microcavity sensor array can be assembled and tested for a single gas at high to moderate concentrations. Finally, a microcavity sensor array can be designed and fabricated at high density and enhanced anti-Stokes reflectivity ($F_{AS}$~100-1000) for multi-gas detection at low concentration (ppm).

Micromirror Fabrication

The fabrication of arrays of micromirrors arranged in a precise geometry should be reliable and repeatable. This is needed to match the micromirror arrays to the microlens arrays for excitation laser focusing (FIGS. 2A-2B), and also to achieve a distribution of cavity parameters that is as homogeneous as possible. A submicron-accuracy x-y-z positioning platform can be obtained and employed to scan a wafer exposed to laser ablation pulses. This upgrade to the current inventor's existing laser ablation system [20], which is incorporated herein by reference, together with correct alignment and automation can permit achievement of accuracy of micromirror positioning to 0.1 microns over a sample size of 1 cm×1 cm. Microlens arrays can be obtained/purchased externally; any suitable microlens array can be used.

Design of Distributed Bragg Reflector Stacks

Optical coatings for micromirror arrays can be obtained (ion beam sputtering by ADVANCED THIN FILMS, Inc.) according to frequency-dependent and phase-dependent reflectivity specifications. The semiconductor epiwafers, which include both gain layers and distributed Bragg reflector layers (DBRs) can also be obtained (INNOLUME, IQE). Because laser light need not be coupled out of the microcavities, both the dielectric and epitaxial DBR stacks can be designed with excess quarter-wave pairs (that is, a minimum transmission is not needed), thus drastically relaxing the complexity of the stacks. Despite the expense of a single fabrication run (near $10,000 for either method), a large number of samples can be obtained per run, easing characterization and assembly troubleshooting. An important specification may be associated with the reflectivity and gain parameters of the epiwafers to match a desired pump fluence. High-power planar VECSEL arrays can be obtained (PRINCETON OPTRONICS) for non-resonant excitation at a level of 1-10 mW per microcavity. Achieving optimal point of operation may require trial/error with both quantum well and quantum dot active layers [3,4,5,19].

Assembly, Characterization and Image Processing

Working primarily with well-characterized test gases, concentration dependent measurements can provide a route for calibration protocols (CARS signal is in general nonlinear with concentration). Image acquisition under length scanning can be characterized and image processing applied to retrieve as precise as possible concentration information from mixtures, primarily in ambient, atmospheric air. Modest pressurization may also be investigated to explore further possibilities in signal enhancement.

REFERENCES

1. B. Petrak, N. Djeu, and A. Muller, "Purcell Enhanced Raman Scattering from Atmospheric Gases in a High-Finesse Microcavity," Phys. Rev. A 89, 023811 (2014).
2. B. Petrak, N. Djeu, and A. Muller, "Coherent Anti-Stokes Raman Scattering in a High-Finesse Microcavity," Opt. Express 22, 21999 (2014).
3. A. Muller, C. K. Shih, J. Ahn, D. Gazula, and D. G. Deppe, "High Q (33 000) all-epitaxial microcavity for quantum dot vertical-cavity surface-emitting lasers and quantum light sources", Appl. Phys. Lett. 88, 031107 (2006).
4. G. Zhao, Y. Zhang, D. G. Deppe, K. Konthasinghe, and A. Muller, "Buried heterostructure vertical-cavity surface-emitting laser with semiconductor mirrors," Appl. Phys. Lett. 101, 101103 (2012).
5. A. Muller, D. Lu, J. Ahn, D. Gazula, S. Quadery, S. Freisem, D. G. Deppe and C. K. Shih, "Buried All-Epitaxial Microcavity for Cavity-QED with Quantum Dots," Nano Lett. 6, 2920 (2006).
6. A. Muller, E. B. Flagg, J. Lawall, and G. S. Solomon, "Ultrahigh finesse Fabry-Perot microcavity with small mode volume," Optics Lett. 35, 2293 (2010).
7. A. Muller, E. B. Flagg, M. Metcalfe, J. Lawall, and G. S. Solomon, "Coupling an epitaxial quantum dot to a fiber-based external-mirror microcavity," Appl. Phys. Lett. 95, (2009).
8. N. Djeu and A. Muller, "Microcavity Raman Sensor and Method of Use," Non-provisional Patent, U.S. Pat. No. 8,599,373, published: Dec. 3, 2013.
9. N. Djeu and A. Muller, "Dual-gas microcavity Raman sensor and method of use," Non-provisional Patent, Publication Number U.S. Pat. No. 8,736,835, published: May 27, 2014.
10. A. N. Martin, G. R. Farquar, M. Frank, E. E. Gard, and D. P. Fergenson, "Single-Particle Aerosol Mass Spectrometry for the Detection and Identification of Chemical Warfare Agent Stimulants," Analytical Chemistry 79, 6368 (2007).
11. R. A. McGill, V. K. Nguyen, R. Chung, R. E. Shaffer, D. DiLella, J. L. Stepnowski, T. E. Mlsna, D. L. Venezky, and D. Dominguez, "The "NRL-SAWRHINO": a nose for toxic gases," Sensors and Actuators B: Chemical 65, 10 (2000).
12. A. Yariv, "Quantum Electronics," 3rd edition, (New York, Wiley, 1989).
13. F. Cairo, F. De Martini, and D. Murra, "QED-vacuum confinement of inelastic quantum scattering at optical frequencies: A new perspective in Raman spectroscopy," Phys. Rev. Lett. 70, 1413 (1993).
14. A. Fainstein and B. Jusserand, "Phonons in semiconductor planar microcavities: A Raman scattering study," Phys. Rev. B 54, 11505 (1996).
15. A. Muller, E. B. Flagg, J. R. Lawall, and G. S. Solomon, "Ultrahigh-finesse, low-mode-volume Fabry Perot microcavity," Opt. Lett. 35, 2293 (2010).
16. Y. Colombe, T. Steinmetz, G. Dubois, F. Linke, D. Hunger, and J. Reichel, "Strong atom-field coupling for Bose-Einstein condensates in an optical cavity on a chip," Nature 450, 272 (2007).
17. H. Xu, E. J. Bjerneld, M. Kall, and L. Borjesson, "Spectroscopy of Single Hemoglobin Molecules by Surface Enhanced Raman Scattering," Phys. Rev. Lett. 83, 4357 (1999).
18. S. Zaitsu, H. Izaki, and T. Imasaka, "Phase-Matched Raman-Resonant Four-Wave Mixing in a Dispersion-Compensated High-Finesse Optical Cavity," Phys. Rev. Lett. 100, 073901 (2008).
19. M. Mangold, V. J. Wittwer, O. D. Sieber, M. Hoffmann, I. L. Krestnikov, D. A. Livshits, M. Golling, T. Suidmeyer, and U. Keller, "VECSEL gain characterization," Opt. Express 20, 4136 (2012).
20. B. Petrak, K. Konthasinghe, S. Perez, and A. Muller, "Feedback-controlled laser fabrication of micromirror substrates," Rev. Sci. Instrum. 82, 123112 (2011).
21. D. Moore, "Recent Advances in Trace Explosives Detection Instrumentation," Sensing and Imaging: An International Journal 8, 9 (2007).

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

Glossary of Claim Terms

About or approximate: this term is used herein to refer to approximately or nearly and in the context of a numerical value or range set forth means ±15% of the numerical. In an embodiment, the term "about" can include traditional rounding according to significant figures of the numerical value. In addition, the phrase "about 'x' to 'y'" includes "about 'x' to about 'y'".

Dielectric coating: This term is used herein to refer to a "Bragg stack" of dielectric layers deposited by thin film deposition methods, preferably ion-beam sputtering.

Excitation laser: This term is used herein to refer to a non-resonant light source that is directed to a gain layer within a microcavity, such as to create a population inversion in that layer for lasing.

High reflectivity near Raman shifted signals: This term is used herein to refer to a high reflectivity of a dielectric coating for light with a frequency coinciding with the frequency of the laser minus the Raman shift associated with a particular rovibrational transition in a specific chemical species.

High-reflector micromirror: This term is used herein to refer to a mirror formed of a substantially planar surface or a curved surface of microscopical lateral extent.

Laser focusing component: This term is used herein to refer to any suitable structure that is capable of directing the light beam from the laser source toward the microcavities disposed within the current invention.

Microcavity length: This term is used herein to refer to a distance between micromirrors along the microcavities formed therebetween.

Microlens array: This term is used herein to refer to an arrangement of small, transmissive optical devices, each of which is capable of focusing a light beam toward the microcavities disposed within the current invention.

Multifluid analysis: This term is used herein to refer to the examination or breakdown of various species of interest within a plurality of fluids.

Raman emission signal detector: This term is used herein to refer to a device that detects the intensity of light associated with a specific Raman shift in order to determine the presence of a chemical entity within a sample.

Residual laser pump light: This term is used herein to refer to any unwanted wavelengths of light that can be filtered out.

Sample: This term is used herein to refer to a fluid to be analyzed for its chemical composition.

Secondary filter: This term is used herein to refer to any suitable optical device that can selectively transmit light beams of different wavelengths prior to receipt by the Raman emission signal detector.

Semiconductor mirror: This term is used herein to refer to a micromirror in which the reflective coating and/or gain layers are made of semiconductor materials.

Species of interest: This term is used herein to refer to a chemical entity, the concentration of which within a sample is desired.

Stochastic: This term is used herein to refer to an analysis or outcome that is randomly determined depending on the potentially-unknown contents of the sample being tested.

Ultrahigh finesse: This term is used herein to refer to a relative level of a microcavity's free spectral range divided by the bandwidth of its resonances. Finesse is determined by the microcavity's losses and independent of the microcavity length.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A horizontally-scaled Raman sensor for chemical analysis of a fluid, where the concentration of multiple chemical species of interest in a sample can be detected simultaneously, said sensor comprising:

a first high-reflector micromirror having a substantially planar surface;

an array of second high-reflector micromirrors each having a curved concave surface, wherein a longitudinal extent of said substantially planar surface is substantially parallel to a longitudinal extent of said curved surface, a channel formed between said first high-reflector micromirror and said array of second high-reflector micromirrors, said sample following a path of travel through said channel and along said substantially planar and curved surfaces;

an array of ultrahigh finesse microcavities formed between said substantially planar surface and each concave micromirror, said array of microcavities each having a microcavity length equal to the distance between said substantially planar surface of said first high-reflector micromirror and said curved surface of said each second high-reflector micromirror;

an excitation laser positioned to emit a light beam incident upon said first high-reflector micromirror and said each second high-reflector micromirror;

a Raman emission signal detector positioned to receive an array of Raman shifted emission signals in order to detect a concentration of a species of interest within said sample that is disposed between said substantially planar surface of said first high-reflector micromirror and said curved surface of said array of second high-reflector micromirrors, wherein said microcavities enhance a magnitude of said Raman shifted emission signals, said first high-reflector micromirror and said each second high-reflector micromirror each exhibiting a high reflectivity of greater than about 99.9% both at a frequency of said light beam emitted by said excitation laser and at a frequency of a Raman-shifted signal of said species of interest, whereby at least one of said array of second high-reflector micromirrors is resonant with a frequency of said excitation laser frequency and doubly-resonant with said Raman-shifted signal of said species of interest, whereby said species of interest can be detected at concentrations of parts-per-million or less.

2. A sensor as in claim 1, wherein said first high-reflector micromirror is a semiconductor mirror.

3. A sensor as in claim 2, wherein said first high-reflector micromirror and said each second high-reflector micromirror are dielectrically coated.

4. A sensor as in claim 2, further comprising gain layers, including quantum wells or quantum dots, are present within said semiconductor micromirror.

5. A sensor as in claim 1, further comprising a laser focusing component positioned between said excitation laser and said first high-reflector micromirror to focus or mode match said light through said microcavities.

6. A sensor as in claim 5, wherein said laser focusing component is a microlens array having a curvature that matches said first and second micromirrors to said microlens array.

7. A sensor as in claim 1, further comprising a secondary filter that removes any residual laser pump light, said secondary filter positioned between said Raman emission signal detector and said first and second micromirrors.

8. A sensor as in claim 1, wherein said microcavity length is tunable piezoelectrically.

9. A sensor as in claim 1, wherein said sample is selected from the group consisting of a gas and a liquid.

10. A sensor as in claim 1, wherein said microcavity length is about 1 μm to about 10 μm.

11. A sensor as in claim 1, wherein said excitation laser is an array of vertical-external-cavity surface-emitting lasers.

12. A sensor as in claim 1, wherein said excitation laser is a non-resonant laser.

13. A sensor as in claim 1, wherein said array of second high-reflector microcavities includes about 10,000-1,000,000 microcavities on a 1 cm$^2$ area.

14. A sensor as in claim 1, wherein said Raman emission signal detector includes image processing that yields a signal with magnitude that scales with the number of microcavities in said array of microcavities.

15. A sensor as in claim 1, wherein said array of second high-reflector micromirrors are disposed directly adjacent to one another, such that said array of microcavities are adjacent to one another also.

16. A sensor as in claim 1, wherein a radius of curvature of said curved concave surface of said each second high-reflector micromirror is smaller than a distance between adjacent curved concaved surfaces.

17. A sensor as in claim 1, wherein said Raman emission signal detector is a charge-coupled device.

18. A horizontally-scaled Raman sensor for chemical analysis of a fluid, where the concentration of multiple chemical species of interest in a gas or liquid sample can be detected simultaneously, said sensor comprising:
- a first high-reflector semiconductor micromirror having a substantially planar surface;
- an array of second high-reflector micromirrors each having a curved concave surface, wherein said first high-reflector micromirror and said each second high-reflector micromirror are dielectrically coated,
- wherein a longitudinal extent of said substantially planar surface is substantially parallel to a longitudinal extent of said curved surface,
- wherein said array of second high-reflector microcavities includes about 10,000-1,000,000 microcavities on an approximately 1 cm$^2$ area,
- wherein a radius of curvature of said curved concave surface of said each second high-reflector micromirror is smaller than a distance between adjacent curved concaved surfaces;
- a channel formed between said first high-reflector micromirror and said array of second high-reflector micromirrors, said sample following a path of travel through said channel and along said substantially planar and curved surfaces;
- an array of ultrahigh finesse microcavities formed between said substantially planar surface and each concave micromirror, said array of microcavities each having a microcavity length equal to the distance between said substantially planar surface of said first high-reflector micromirror and said curved surface of said each second high-reflector micromirror,
- wherein said microcavity length is tunable piezoelectrically, wherein said microcavity length is about 1 μm to about 10 μm,
- wherein said array of second high-reflector micromirrors are disposed directly adjacent to one another, such that said array of microcavities are adjacent to one another also,
- an excitation laser positioned to emit a light beam incident upon said first high-reflector micromirror and said each second high-reflector micromirror, wherein said excitation laser is a non-resonant laser or an array of vertical-external-cavity surface-emitting lasers;
- a laser focusing component positioned between said excitation laser and said first high-reflector micromirror to focus or mode match said light through said microcavities, wherein said laser focusing component is a microlens array having a curvature that matches said first and second micromirrors to said microlens array;
- a charge-coupled device positioned to receive an array of Raman shifted emission signals in order to detect a concentration of a species of interest within said sample that is disposed between said substantially planar surface of said first high-reflector micromirror and said curved surface of said array of second high-reflector micromirrors, wherein said microcavities enhance a magnitude of said Raman shifted emission signals,
- wherein said charge-coupled device includes image processing that yields a signal with magnitude that scales with the number of microcavities in said array of microcavities; and
- a secondary filter that removes any residual laser pump light, said secondary filter positioned between said charge-coupled device and said first and second micromirrors,
- said first high-reflector micromirror and said each second high-reflector micromirror each exhibiting a high reflectivity of greater than about 99.9% both at a frequency of said light beam emitted by said excitation laser and at a frequency of a Raman-shifted signal of said species of interest;
- whereby at least one of said array of second high-reflector micromirrors is resonant with a frequency of said excitation laser frequency and doubly-resonant with said Raman-shifted signal of said species of interest,
- whereby said species of interest can be detected at concentrations of parts-per-million or less.

* * * * *